United States Patent [19]

Postle

[11] 4,359,522
[45] Nov. 16, 1982

[54] PHOTOGRAPHIC ELEMENT CONTAINING A UV-FILTER LAYER

[75] Inventor: Stephen R. Postle, Brentwood, England

[73] Assignee: Ciba-Geigy AG, Basel, Switzerland

[21] Appl. No.: 291,696

[22] Filed: Aug. 10, 1981

[30] Foreign Application Priority Data

Aug. 29, 1980 [GB] United Kingdom ................ 8028070

[51] Int. Cl.³ .............................................. G03C 1/78
[52] U.S. Cl. .................................... 430/512; 430/931; 523/135
[58] Field of Search .......................... 430/512, 931, 4; 350/1.1; 523/135

[56] References Cited

U.S. PATENT DOCUMENTS

| 4,052,216 | 10/1977 | Sobel et al. | 430/931 |
| 4,245,018 | 1/1981 | Hara et al. | 430/512 |
| 4,309,500 | 1/1982 | Shishido | 430/515 |

*Primary Examiner*—Jack P. Brammer
*Attorney, Agent, or Firm*—Joseph G. Kolodny

[57] ABSTRACT

Light-sensitive photographic material which contains as a uv-filter layer a non-light sensitive layer comprising a compound of the formula

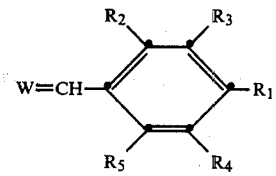

wherein W is the residue of an oxazolone, isoxazolone or pyrazolone ring, $R_1$, $R_2$ and $R_5$ are each hydrogen or halogen or $-OCOR_{10}$ wherein $R_{10}$ is an optionally substituted alkyl or alkoxy, alkaryl or aryl, and $R_3$ and $R_4$ are each hydrogen or alkoxy.

These compounds exhibit a very sharp cut-off point at about 400 nm.

12 Claims, 2 Drawing Figures

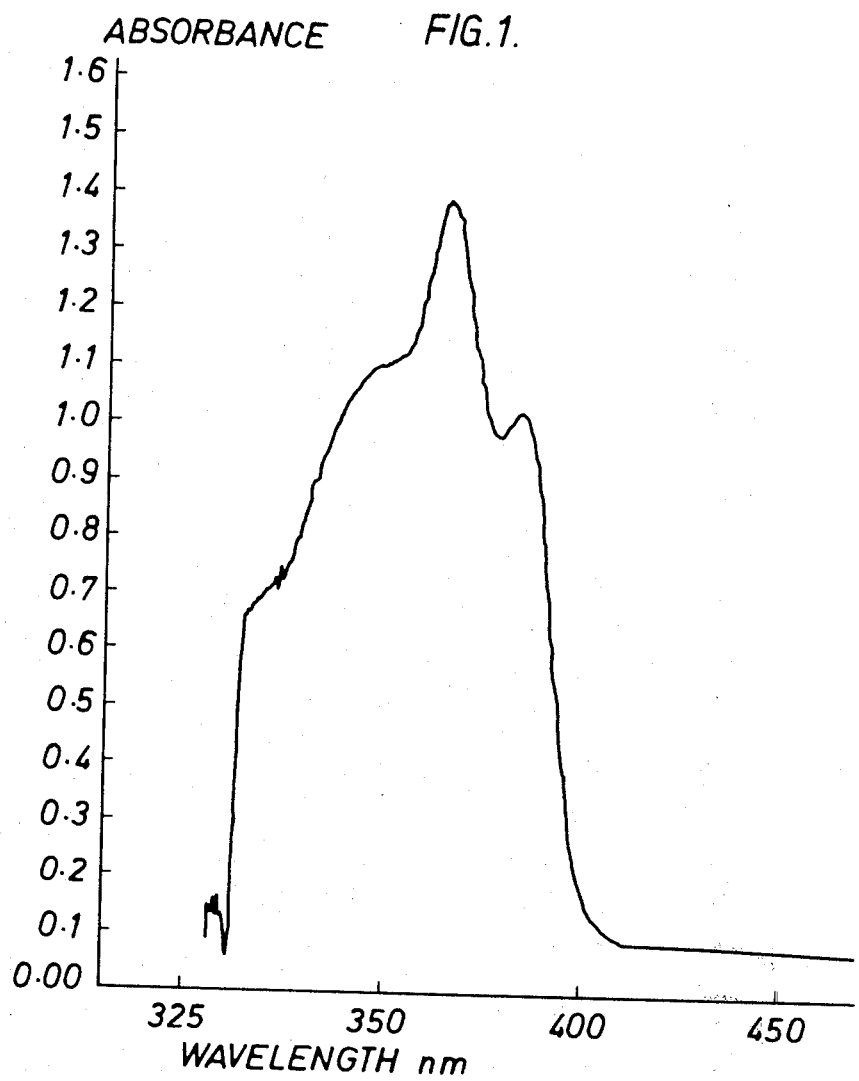

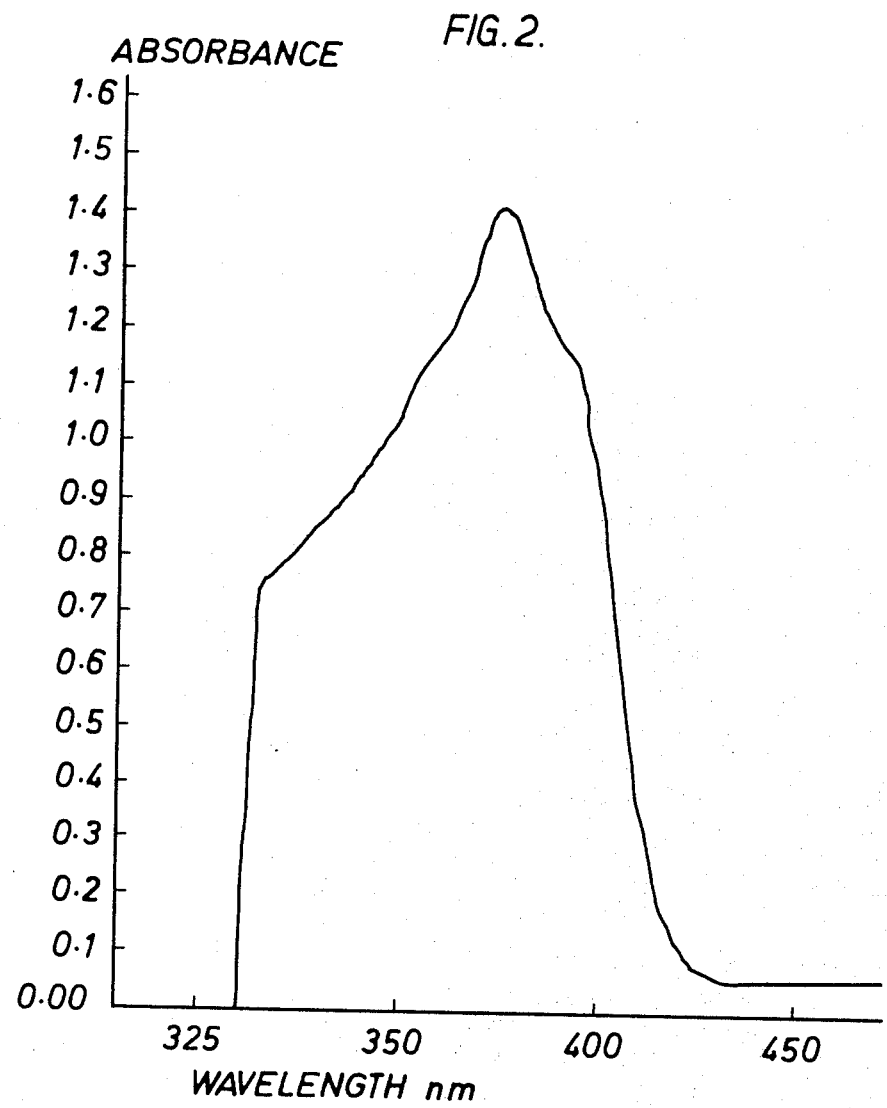

PHOTOGRAPHIC ELEMENT CONTAINING A UV-FILTER LAYER

The present invention relates to light-sensitive photographic material which comprises an ultra-violet light (uv) absorbing layer.

It is common in photographic materials and in particular in colour photographic materials to provide a uv-absorbing layer to minimise the tendency of high-light areas which are not in fact blue from appearing blue in the final print. Various uv-absorbing compounds have been used for this purpose and their chief requirement is that they absorb all actinic light below 400 nm but have a very sharp cut-off point at about 400 nm. It has now been found that a class of known compounds can be used in uv-absorbing layers because they have such a sharp cut-off point.

According to the present invention there is provided a light-sensitive photographic material which contains as a uv-filter layer a non-light sensitive layer comprising a compound of the formula

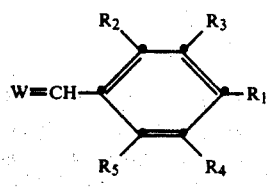

(1)

wherein $R_1$, $R_2$ and $R_5$ are each hydrogen or halogen or a group of the formula $-OCOR_{10}$, wherein $R_{10}$ is optionally substituted alkyl or alkoxy having from 1 to 30 carbon atoms, or is optionally substituted alkaryl or aryl, $R_3$ and $R_4$ are each hydrogen or alkoxy having 1 to 6 carbon atoms, W is a residue of the formula

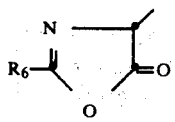

(2)

where $R_6$ is optionally substituted phenyl, or W is a residue of the formula

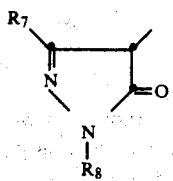

(3)

wherein $R_7$ is alkyl having 1 to 6 carbon atoms, aryl, carboxylic acid or alkoxycarbonyl, wherein the alkoxy moiety contains 1 to 6 carbon atoms and $R_8$ is aryl or a residue of the formula

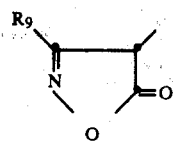

(4)

wherein $R_9$ is alkyl having 1 to 6 carbon atoms or optionally substituted aryl.

Another object of the present invention is a process for the manufacture of the inventive photographic material.

The substituents $R_1$, $R_2$ and $R_5$ in compounds of the formula (1) are independently of each other hydrogen, halogen such as chlorine or bromine, or are an acyloxy group of the formula $-OCOR_{10}$. $R_{10}$ in this residue is alkyl having from 1 to 30 carbon atoms. These alkyl groups can be straight or branched chain. Suitable radicals are methyl, ethyl, propyl, i-propyl, butyl, i-butyl, t-butyl, amyl, t-amyl (1,1-dimethylpropyl), 1,1,3,3-tetramethylbutyl, 1-methylethylpentyl, hexyl, 1-methylpentyl, neopentyl, 1-, 2- or 3-methylhexyl, heptyl, n-octyl, t-octyl, 2-ethylhexyl, n-nonyl, i-nonyl, t-nonyl, decyl, t-decyl and undecyl; further dodecyl, tetradecyl, hexadecyl, octadecyl, nonadecyl, eicosyl, docosyl, tetracosyl, hexacosyl, octacosyl, triacontyl and branched isomers thereof. Preferred are those straight or branched chain alkyl groups having from 5 to 30, especially from 10 to 30 carbon atoms. The alkyl groups $R_{10}$ are optionally substituted by alkoxy having from 1 to 15, preferably 1 to 6 carbon atoms. Species of such alkoxy groups are derivable from the alkyl moieties listed above for $R_{10}$. A further suitable substituent on the alkyl groups $R_{10}$ is acyloxy such as $-OCOR$ wherein R is alkyl having 1 to 10, preferably 1 to 4 carbon atoms. Radicals of suitable alkyl groups ($C_1-C_{10}$ and $C_1-C_4$, respectively) are listed above in the definition of $R_{10}$. Preferred is also an alkyl substituted phenoxy group as a substituent for the alkyl radicals $R_{10}$. These phenoxy groups contain alkyl chains having 1 to 15, preferably 1 to 8 carbon atoms and examples are listed above in the definition of $R_{10}$. In the meaning of alkoxy, $R_{10}$ contains 1 to 30 carbon atoms. Radicals of such alkoxy groups are those derivable from the alkyl moieties listed above for $R_{10}$. Preferred alkoxy groups have 5 to 30, more preferably 10 to 30 carbon atoms. $R_{10}$ denotes further alkaryl wherein the alkyl part contains 1 to 15, preferably 1 to 8 carbon atoms—radicals are mentioned above—and the aryl part is represented by a naphthyl or preferably by a phenyl ring. As an aryl group, $R_{10}$ denotes naphthyl or preferably phenyl. These groups are optionally further substituted by halogen, preferably chlorine or bromine, and alkoxy having form 1 to 15, preferably 1 to 8, carbon atoms, species thereof are referred to above in the definitions of $R_{10}$.

The substituent $R_1$ is preferably the acyloxy group of the formula $-OCOR_{10}$, wherein $R_{10}$ has the meaning indicated above. $R_2$ and $R_5$ are preferably hydrogen.

$R_3$ and $R_4$ are independently of each other hydrogen or alkoxy having 1 to 6 carbon atoms. Suitable alkoxy groups are methoxy, ethoxy, butoxy and hexoxy. Preferred are methoxy and ethoxy. Most preferably, $R_3$ and $R_4$ are independently of each other hydrogen or methoxy.

The substituent W in the compounds of formula (1) denotes an oxazolonyl group of the formula

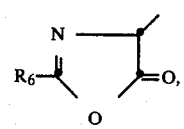

(2)

wherein $R_6$ is phenyl, optionally substituted by halogen such as chlorine or bromine or alkoxy having 1 to 15, preferably 1 to 8 carbon atoms. Suitable alkoxy groups are mentioned above in the definitions of $R_{10}$.

W represents further a pyrazolonyl group of the formula

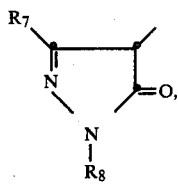  (3)

wherein $R_7$ is alkyl having 1 to 6 carbon atoms such as methyl, ethyl, propyl, butyl, t-butyl, pentyl or hexyl. Further, $R_7$ is aryl such as naphthyl or phenyl, optionally substituted by halogen, for example bromine or chlorine, or alkoxy having from 1 to 15 carbon atoms. For suitable alkoxy groups see above in the definitions of $R_{10}$. $R_7$ denotes further carboxylic acid (—COOH) or alkoxycarbonyl, wherein the alkoxy moiety contains from 1 to 6 carbon atoms. Suitable alkoxy groups are the analogs of the alkyl radicals mentioned for $R_7$. $R_8$ in the pyrazolyl residue of formula (3) denotes aryl, preferably naphthyl or phenyl, and more preferably phenyl, optionally substituted by halogen, such as chlorine or bromine, or alkoxy having 1 to 15 carbon atoms. For suitable species see above in the definitions of $R_{10}$. Further $R_8$ is isoxazolonyl of the formula

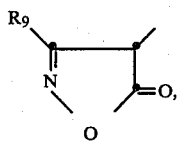  (4)

wherein $R_9$ is alkyl having 1 to 6 carbon atoms—as represented by $R_7$—or aryl, such as naphthyl or phenyl, preferably phenyl, optionally substituted by halogen, preferably chlorine or bromine, or alkoxy having 1 to 15 carbon atoms. Preferred radicals are referred to above in the definitions of $R_{10}$.

In a preferred light-sensitive photographic material, $R_1$, $R_2$ and $R_5$ in a compound of the formula (1) denote each hydrogen, chlorine, bromine or a group of the formula —OCOR$_{100}$, wherein $R_{100}$ is alkyl having 1 to 30 carbon atoms optionally substituted by alkoxy having 1 to 15 carbon atoms, acyloxy having 2 to 11 carbon atoms or phenoxy which is optionally substituted by alkyl having 1 to 15 carbon atoms, or $R_{100}$ is alkoxy having 1 to 30 carbon atoms or phenyl or naphthyl substituted by alkyl having 1 to 15 carbon atoms, chlorine, bromine or alkoxy having 1 to 15 carbon atoms.

More preferably, $R_1$, $R_2$ and $R_5$ are each hydrogen, chlorine or a group of the formula —OCOR$_{101}$, wherein $R_{101}$ is alkyl having 5 to 30 carbon atoms, optionally substituted by alkoxy having 1 to 6 carbon atoms, acyloxy having 2 to 5 carbon atoms or phenoxy which is optionally substituted by alkyl having 1 to 15 carbon atoms, or $R_{101}$ is alkoxy having 5 to 30 carbon atoms or phenyl substituted by alkyl having 1 to 8 carbon atoms, chlorine or alkoxy having 1 to 8 carbon atoms.

Very suitable light-sensitive photographic material contains a compound of the formula (1) wherein $R_1$, $R_2$ and $R_5$ are each hydrogen or a group of the formula —OCOR$_{102}$, wherein $R_{102}$ is alkyl having 10 to 30 carbon atoms, optionally substituted by phenoxy which is optionally substituted by alkyl having 1 to 15 carbon atoms.

Preferably, a light-sensitive photographic material is used, wherein W is a residue of the formula

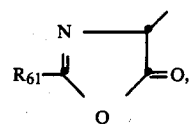  (6)

wherein $R_{61}$ is phenyl optionally substituted by chlorine or alkoxy having 1 to 15 carbon atoms, or W is a residue of the formula

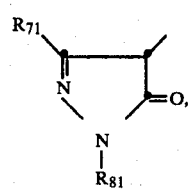  (7)

wherein $R_{71}$ is methyl, ethyl, butyl, phenyl which is optionally substituted by chlorine or alkoxy having 1 to 15 carbon atoms, or $R_{71}$ is —COOH or alkoxycarbonyl having 2 or 3 carbon atoms, and $R_{81}$ is phenyl optionally substituted by chlorine or a residue of the formula

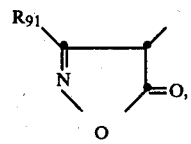  (8)

wherein $R_{91}$ is alkyl having 1 to 6 carbon atoms or phenyl optionally substituted by chlorine.

In light-sensitive photographic material of interest, W is a residue of the formula

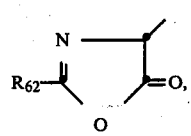  (9)

wherein $R_{62}$ is phenyl optionally substituted by chlorine or alkoxy having 1 to 8 carbon atoms.

Mostly preferred is a light-sensitive photographic material which comprises a compound of the formula

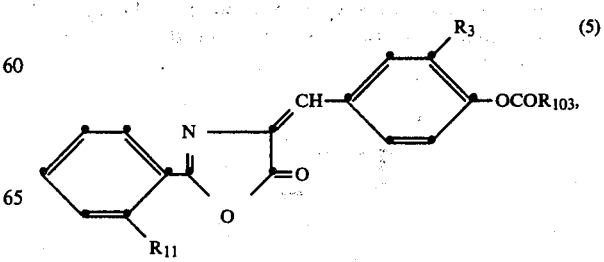  (5)

wherein $R_{11}$ is hydrogen or chlorine, $R_{103}$ is alkyl having from 10 to 30 carbon atoms and $R_3$ is as defined in claim 1.

The preferred compounds of formula (1) are those, wherein W is an oxazolone ring of formulae (2), (6) or (9).

Preferably the photographic material is a silver halide material which comprises in the supercoat layer the compounds of formula (1). Most preferably the supercoat layer is a non-light sensitive gelatin layer and the compounds of formula (1) have been added to the aqueous gelatin coating solution from which the supercoat is prepared either an an aqueous solution or as an organic solvent solution wherein the organic solvent is water-miscible. Alternatively the compounds of formula (1) may be present in the supercoat layer as an oil dispersion or as a solid dispersion.

The coating weight of the compounds of formula (1) in the uv-filter layer is usually within the range of 0.1–40, preferably 0.5–20 $mg/dm^2$.

The compounds of formula (1) when formulated in a uv-filter layer absorb all uv-light up to and including 400 nm light but their absorption does not extend appreciably into the visible region of the spectrum. Thus the compounds are either colourless or very pale yellow. They have no appreciable visible density at the coating weight usually employed for filter layers.

Closely related compounds to those of formula (1), for example compounds having the same general formula (1) but wherein $R_1$ is an alkoxy or aryloxy group, do not display the same sharp cut-off point in the absorption spectrum as that displayed by the compounds of formula (1). Thus such closely related compounds to those of the present invention are of a distinctly yellow colour and thus could not be employed in the uv-filter layer in colour photographic material.

Compounds of formula (1) are known compounds and may be synthesised from the appropriate heterocyclic compound and an appropriate aldehyde as described in "Pyrazolones, Pyrazolidones and Derivatives", published by R. N. Wiley and P. Wiley, Interscience, N.Y. 1964. For example the compounds of formula (5) may be prepared by reacting the appropriate hippuric acid with benzaldehyde as described for example by Y. S. Rao, "Journal of Organic Chemistry", (1976), vol 41, p. 722; H. E. Carter, "Organic Reactions", (1974), vol. 3, p. 199; J. W. Cornforth, "Chemistry of Penicillin", edited by M. T. Clarke, J. R. Johnson and R. Robinson, Princeton University Press, Princeton, N.J., (1948), p. 688; E. Baltazzi, "Quarterly Reviews of the Chemical Society", (1955), vol. 9, p. 150; J. W. Cornforth, "Heterocyclic Compounds", edited by R. C. Elderfield, Wiley, N.Y., (1957), vol. 9, p. 298; R. Fuller, "Advances in Heterocyclic Chemistry", (1965), vol. 4, p. 75; W. Steglich, "Fortschritt für Chemische Forschung", (1969), vol. 12, p. 77; Particularly preferred methods of preparation are those of E. Baltazzi and R. Robinson, "Chemistry and Industry", (1954), p. 191, wherein the hippuric acid and benzaldehyde are condensed together in acetic acid and tetrahydrofuran, employing lead-(II)-acetate as catalyst, and of M. Crawford and W. I. Little, "Journal of the Chemical Society", (1959), p. 729, wherein the hippuric acid is precondensed to a 2-aryl-oxazol-5-one and this is fused with the appropriate benzaldehyde.

The following preparations will serve to illustrate the preparation of compounds of formula (1).

PREPARATION I

Preparation of the compound of the formula

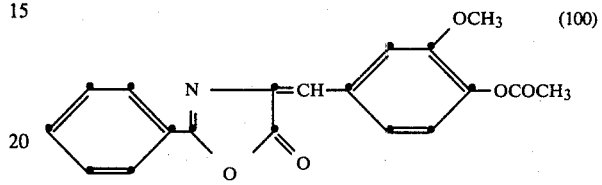

4-Hydroxybenzaldehyde (6.1 g) and hippuric acid (8.95 g) are heated with sodium acetate (4.1 g) in acetic anhydride (50 ml) at 100° C. for two hours. The crude product crystallises from the cooled mixture, and is recrystallised from toluene. Yield=12.0 g.

The absorption spectrum of this uv-absorber is shown in FIG. 1, in acetone solution ($\epsilon_{350}=2.9\times10^4$, $\epsilon_{364}=3.7\times10^4$, $\epsilon_{383}=2.7\times10^4$).

PREPARATION II

Preparation of the compound of the formula

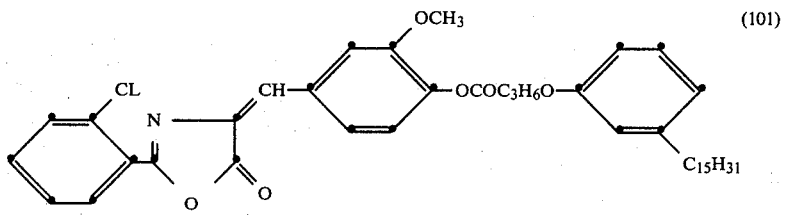

2-Chlorohippuric acid (2.14 g) and 3-methoxy-4-4'-(3''-pentadecylphenoxy)butyryloxy benzaldehyde (5.24 g) are heated together with lead acetate (1.63 g) in tetrahydrofuran (24 ml) and acetic anhydride (3 ml) at reflux for 4 hours. The cooled mixture is diluted with water (200 ml) and the yellow oil extracted with chloroform (2×25 ml). These extracts are washed with water (200 ml) and evaporated to give a yellow oil. This is scratched under methanol and recrystallised from methanol. Yield=3.42 g.

The absorption spectrum of this uv absorver is shown in FIG. 2. ($\epsilon_{374}=2.37\times10^4$; $\epsilon_{392}=1.93\times10^4$) in acetone solution.

EXAMPLE

A photographic silver halide material having a uv-absorbing layer is prepared as follows:

A silver iodobromide emulsion containing 2% iodide to 98% bromide is prepared. A portion of this emulsion which contains 70 mg gelatin and 70 mg silver has dispersed in it 30 mg of the yellow colour coupler of formula

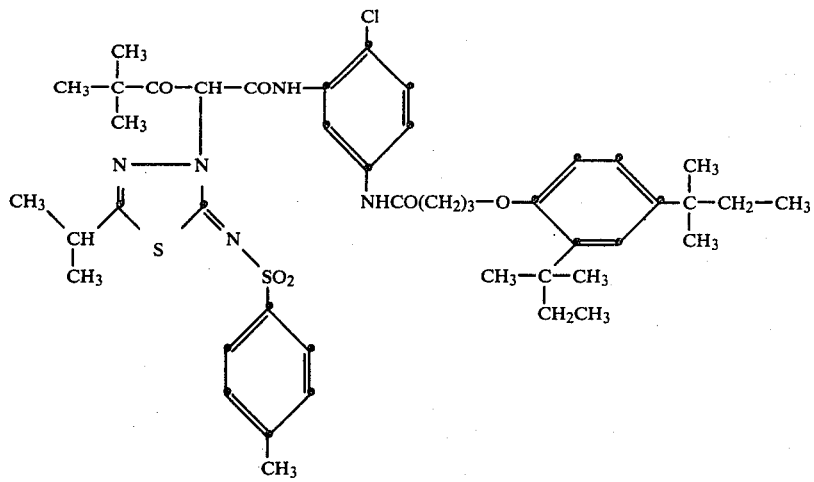

(103)

5-γ{-[2,4-Bis(1,1-dimethylpropyl)phenoxy]-butyramido}-2-chloro-α-[5-isopropyl-2-(4-tolylsulphonylimino)-Δ$^4$-1,3,4-thiadiazolin-2-yl]-α-pivalolylacetanilide in tri-isopropyl phenyl phosphate. The resulting emulsion is coated on to 1 dm$^2$ of subbed polyester support and the coating dried.

On this silver halide emulsion layer there is coated a non-stress layer which comprises compound (100) as a uv-absorber. This layer is prepared as follows.

The following solution is prepared:

| Compound (100) | 1 g |
| --- | --- |
| Di-n-butyl phthalate (DBP) | 1 g |
| Ethyl acetate | 1 g |
| 10% gelatin solution | 8 g |
| 10% anionic wetting agent | 2 ml |
| Distilled water | 2 ml | by dissolving compound (100) in the DBP and ethyl acetate on a hot plate. Then the gelatin solution to which the distilled water and wetting agent has been added is heated to 50° C. The solution of compound (100) is added to the gelatin solution and mixed in an ultra-sonic mixer for two minutes.

A gelatin non-stress layer is prepared containing:

| Gelatin | 0.9 g |
| --- | --- |
| Distilled water | 22.5 g |
| Dispersion of compound (100) as just prepared | 1.73 g |
| 10% wetting agent | 0.7 ml |

0.62 ml of this solution is coated on the 1 dm$^2$ polyester support coated with the silver halide emulsion layer and the coating dried. The gelatin coating weight of the dried non-stress layer is 23.8 mg per 1 dm$^2$ and the coating weight of compound (100) is 2.8 mg per 1 dm$^2$.

A strip of this material (strip A) is taken and exposed with a standard step wedge to a tungsten halogen light source, and processed at 37.8° C. in the following solutions:

| 1. Colour developing developer bath: | | |
| --- | --- | --- |
| Potassium carbonate | 37.5 | g |
| Sodium metabisulphite (anhydrous) | 4.25 | g |
| Potassium iodide | 2.0 | mg |
| Sodium bromide | 1.3 | g |
| Hydroxylamine sulphate | 2.0 | g |
| 4-(N—ethyl-N—β-hydroxyethylamino)-2-methylaniline sulphate | 4.75 | g |
| Water to make up to | 1 | liter. |
| 2. Bleaching | 6½ | minutes |
| bleaching bath: | | |
| Ammonium bromide | 150 | g |
| Ammonium salt of the iron-III-complex of ethylenediamine tetra-acetic acid | 175 | ml |
| Acetic acid (glacial acetic acid) | 10.5 | ml |
| Sodium nitrate | 35 | g |
| Water to make up to | 1 | liter. |
| 3. Washing | 3¼ | minutes |
| 4. Fixing | 6½ | minutes |
| fixing bath: | | |
| Ammonium thiosulphate (50% aqueous) | 16.2 | ml |
| Diethylenetriaminepenta-acetic acid | 1.25 | g |
| Sodium metabisulphite (anhydrous) | 12.4 | g |
| Sodium hydroxide | 2.4 | g |
| Water to make up to | 1 | liter, |
| 5. Washing | 3¼ | minutes |
| 6. Stabilising | | |
| stabiliser bath: | | |
| Formaldehyde (35% aqueous solution) | 5.0 | ml |
| Water to make up to | 1 | liter. |

A yellow image is obtained showing that the film is sensitive to blue light. Another strip A is exposed briefly to a mercury vapour lamp, with a standard step wedge. After processing as above no image is obtained.

This shows that compound (100) acts as a uv-absorber during the exposure of the photographic material but is also present in the processed photographic material and thus would help to preserve the yellow dye image from deterioration caused by uv-light if the processed strip is to be used as a negative in subsequent exposing and printing operations.

A strip of material is then taken by coating the silver halide emulsion layer alone, without the uv-filter layer (strip B). Separate pieces of this are exposed to both the tungsten halogen light source and to the mercury vapour lamp. In each case an image is obtained after processing. This further demonstrates the uv-absorbing nature of the compounds of this invention.

I claim:

1. A light-sensitive photographic element which contains a silver halide emulsion layer and as a uv-filter layer a layer comprising a compound of the formula

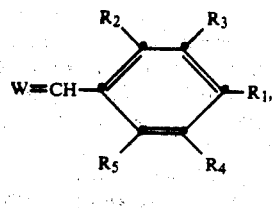

wherein
R$_1$, R$_2$ and R$_5$ are each hydrogen or halogen or a group of the formula —OCOR$_{10}$, wherein R$_{10}$ is optionally substituted alkyl or alkoxy having from 1 to 30 carbon atoms, or is optionally substituted alkaryl or aryl,
R$_3$ and R$_4$ are each hydrogen or alkoxy having 1 to 6 carbon atoms, W is a residue of the formula

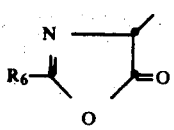

where R$_6$ is optionally substituted phenyl, or W is a residue of the formula

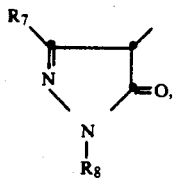

wherein R$_7$ is alkyl having 1 to 6 carbon atoms, aryl, carboxylic acid or alkoxycarbonyl, wherein the alkoxy moiety contains 1 to 6 carbon atoms and R$_8$ is aryl or a residue of the general formula

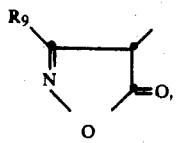

wherein R$_9$ is alkyl having 1 to 6 carbon atoms or optionally substituted aryl.

2. A light-sensitive photographic element according to claim 1, wherein R$_1$, R$_2$ and R$_5$ are each hydrogen, chlorine, bromine or a group of the formula —O—COR$_{100}$, wherein R$_{100}$ is alkyl having 1 to 30 carbon atoms optionally substituted by alkoxy having 1 to 15 carbon atoms, acyloxy having 2 to 11 carbon atoms or phenoxy which is optionally substituted by alkyl having 1 to 15 carbon atoms, or R$_{100}$ is alkoxy having 1 to 30 carbon atoms, or phenyl or naphthyl substituted by alkyl having 1 to 15 carbon atoms, chlorine, bromine or alkoxy having 1 to 15 carbon atoms.

3. A light-sensitive photographic element according to claim 1, wherein R$_1$, R$_2$ and R$_5$ are each hydrogen, chlorine or a group of the formula —OCOR$_{101}$, wherein R$_{101}$ is alkyl having 5 to 30 carbon atoms, optionally substituted by alkoxy having 1 to 6 carbon atoms, acyloxy having 2 to 5 carbon atoms or phenoxy which is optionally substituted by alkyl having 1 to 15 carbon atoms, or R$_{101}$ is alkoxy having 5 to 30 carbon atoms or phenyl substituted by alkyl having 1 to 8 carbon atoms, chlorine or alkoxy having 1 to 8 carbon atoms.

4. A light-sensitive photographic element according to claim 1, wherein R$_1$, R$_2$ and R$_5$ are each hydrogen or a group of the formula —OCOR$_{102}$, wherein R$_{102}$ is alkyl having 10 to 30 carbon atoms, optionally substituted by phenoxy which is optionally substituted by alkyl having 1 to 15 carbon atoms.

5. A light-sensitive photographic element according to claim 1, wherein W is a residue of the formula

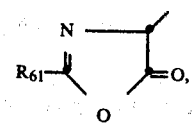

wherein
R$_{61}$ is phenyl optionally substituted by chlorine or alkoxy having 1 to 15 carbon atoms,
or W is a residue of the formula

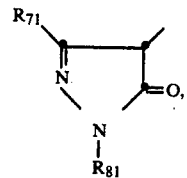

wherein R$_{71}$ is methyl, ethyl, butyl, phenyl which is optionally substituted by chlorine or alkoxy having 1 to 15 carbon atoms, or R$_{71}$ is —COOH or alkoxycarbonyl having 2 to 3 carbon atoms, and R$_{81}$ is phenyl optionally substituted by chlorine or a residue of the formula

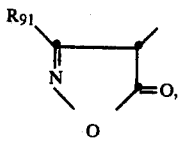

wherein R$_{91}$ is alkyl having 1 to 6 carbon atoms or phenyl optionally substituted by chlorine.

6. A light-sensitive photographic element according to claim 5, wherein W is a residue of the formula

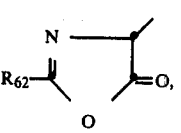

wherein R$_{62}$ is phenyl optionally substituted by chlorine or alkoxy having 1 to 8 carbon atoms.

7. A light-sensitive photographic element according to claim 1, which comprises a compound of the formula

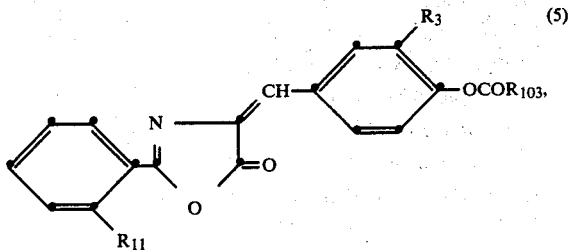

(5)

wherein $R_{11}$ is hydrogen or chlorine, $R_{103}$ is alkyl having from 10 to 30 carbon atoms and $R_3$ is as defined in claim 1.

8. A light-sensitive photographic element according to claim 1 which is silver halide photosensitive material and the compound of formula (1) is present in a supercoat layer.

9. A light-sensitive photographic element according to claim 8 wherein the supercoat layer is a gelatin layer and the compound of formula (1) has been added to an aqueous gelatin supercoat coating solution either as an aqueous solution or as an organic solvent solution wherein the organic solvent is water-miscible.

10. A light-sensitive photographic element according to claim 8 wherein the compound of formula (1) is present in the supercoat layer as an oil dispersion or as a solid dispersion.

11. A light-sensitive photographic element according to claim 1 wherein the compound of formula (1) is present within the range of 0.5–20 mg/dm$^2$.

12. A process for the manufacture of a light-sensitive photographic element according to claim 1, wherein the compound of the formula (1) is incorporated into a non-light sensitive layer of the photographic element.

* * * * *